(12) United States Patent
Saunders et al.

(10) Patent No.: US 11,241,180 B2
(45) Date of Patent: *Feb. 8, 2022

(54) TESTING AND TRAINING APPARATUS

(71) Applicant: Kangatech Pty Ltd., North Melbourne (AU)

(72) Inventors: Steven Wayne Saunders, North Melbourne (AU); David Charles Scerri, North Melbourne (AU)

(73) Assignee: Kangatech Pty Ltd., North Melbourne (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/913,014

(22) Filed: Jun. 26, 2020

(65) Prior Publication Data

US 2020/0323476 A1 Oct. 15, 2020

Related U.S. Application Data

(63) Continuation of application No. 15/631,114, filed on Jun. 23, 2017.

(51) Int. Cl.
| | | |
|---|---|---|
| *A61B 5/22* | (2006.01) | |
| *A61B 5/00* | (2006.01) | |
| *A63B 23/04* | (2006.01) | |
| *A63B 21/002* | (2006.01) | |

(52) U.S. Cl.
CPC ............ *A61B 5/224* (2013.01); *A61B 5/6895* (2013.01); *A63B 21/0023* (2013.01); *A63B 23/04* (2013.01); *A61B 2562/0252* (2013.01); *A63B 2220/50* (2013.01); *A63B 2220/51* (2013.01);

(Continued)

(58) Field of Classification Search
CPC .............. A63B 23/04; A63B 2220/833; A63B 2225/093; A63B 2225/50; A61B 2562/0252

See application file for complete search history.

(56) References Cited

U.S. PATENT DOCUMENTS

| | | |
|---|---|---|
| 3,285,070 A | 11/1966 | McDonough |
| 3,752,144 A | 8/1973 | Weigle |
| 4,333,340 A | 6/1982 | Elmeskog |

(Continued)

FOREIGN PATENT DOCUMENTS

| | | |
|---|---|---|
| CN | 2532882 Y | 1/2003 |
| CN | 201631966 U | 11/2010 |

(Continued)

OTHER PUBLICATIONS

Norbord Hamstring Testing System; Vald Performance; published Jun. 4, 2016; retrieved on Aug. 24, 2017 from https://www.valdperformance.com/nordbord-hamstring-testing-system/.

(Continued)

*Primary Examiner* — Justin N Olamit
(74) *Attorney, Agent, or Firm* — Stevens & Showalter LLP

(57) ABSTRACT

A testing and training apparatus, comprising: an upright frame; an instrumentation support that is supported by the upright frame so as to be adjustable in height; and instrumentation mountable on the instrumentation support. The instrumentation comprises a plurality of force sensors, and is rotatable relative to the upright frame, and the apparatus is controllable to output data signals indicative of force detected by the force sensors.

20 Claims, 13 Drawing Sheets

(52) U.S. Cl.
CPC ... *A63B 2220/833* (2013.01); *A63B 2225/093* (2013.01); *A63B 2225/50* (2013.01)

(56) References Cited

U.S. PATENT DOCUMENTS

| | | | |
|---|---|---|---|
| 4,647,039 A | 3/1987 | Noffsinger | |
| 4,702,108 A | 10/1987 | Amundsen et al. | |
| 4,732,038 A | 3/1988 | DelGiorno et al. | |
| 4,805,455 A | 2/1989 | Delgiorno et al. | |
| 4,972,711 A | 11/1990 | Sanjeev et al. | |
| 5,331,851 A | 7/1994 | Arno et al. | |
| 5,348,519 A | 9/1994 | Prince et al. | |
| 5,662,591 A | 9/1997 | Peindl et al. | |
| 5,711,726 A | 1/1998 | Powers | |
| 5,800,310 A | 9/1998 | Jones | |
| 6,149,550 A | 11/2000 | Shteingold | |
| 6,302,833 B1 | 10/2001 | Ellis et al. | |
| 6,482,139 B1 | 11/2002 | Haag | |
| 7,493,812 B2 * | 2/2009 | Andres | A61B 5/1071 73/379.01 |
| 7,927,262 B2 | 4/2011 | Clark | |
| 8,057,368 B1 | 11/2011 | Lyszczarz | |
| 8,221,295 B2 | 7/2012 | Wilkins et al. | |
| 8,491,446 B2 | 7/2013 | Hinds et al. | |
| 8,632,444 B2 | 1/2014 | McBride et al. | |
| 9,114,272 B2 | 8/2015 | Fowler | |
| 9,295,871 B2 | 3/2016 | Luedeka | |
| 9,694,229 B2 | 7/2017 | Taft | |
| 2004/0002410 A1 | 1/2004 | Steinbach et al. | |
| 2004/0014566 A1 | 1/2004 | Kao | |
| 2004/0110602 A1 | 6/2004 | Feldman | |
| 2008/0119763 A1 | 5/2008 | Wiener | |
| 2011/0224583 A1 | 9/2011 | Lequeux | |
| 2013/0023390 A1 | 1/2013 | Ree | |
| 2013/0281261 A1 | 10/2013 | Gatherer | |
| 2015/0297128 A1 | 10/2015 | Shield et al. | |
| 2016/0107025 A1 | 4/2016 | Chang | |

FOREIGN PATENT DOCUMENTS

| | | | |
|---|---|---|---|
| CN | 201691940 U | 1/2011 | |
| CN | 201759570 U | 3/2011 | |
| CN | 201847886 U | 6/2011 | |
| CN | 102306029 A | 1/2012 | |
| CN | 102327174 A | 1/2012 | |
| CN | 202699974 U | 1/2013 | |
| CN | 103801050 A | 5/2014 | |
| CN | 104146777 A | 11/2014 | |
| DE | 19718793 A1 | 11/1997 | |
| DE | 29612368 U1 | 12/1997 | |
| JP | H03159637 A | 7/1991 | |
| WO | 9513015 A1 | 5/1995 | |
| WO | 0126748 A1 | 4/2001 | |
| WO | 2003094732 A1 | 11/2003 | |
| WO | 2007020663 A1 | 2/2007 | |
| WO | 2016160719 A1 | 10/2016 | |
| WO | WO-2017045027 A1 * | 3/2017 | G16H 10/60 |

OTHER PUBLICATIONS

Groinbar Hip Strength Testing System; Vald Performance; published Nov. 1, 2016; retrieved on Aug. 25, 2017 from https://www.valdperformance.com/groinbar-hip-strength-testing-system/.

System 4 Pro; Biodex Medical Systems; published Jun. 12, 2016; retrieved on Aug. 24, 2017 from http://www.biodex.com/physical-medicine/products/dynamometers/system-4-pro.

Screen capture of website as found on the internet archive Wayback Machine; Jun. 21, 2017; Retrieved from internet at https://web.archive.org/web/20170621041335/http://valdperformance.com/groinbar-hip-strength-testing-system/ on May 15, 2019.

Justin N. Olamit; Office Action; U.S. Appl. No. 15/631,114; dated Mar. 26, 2020; United States Patent and Trademark Office; Alexandria, Virginia.

Justin N. Olamit; Office Action; U.S. Appl. No. 15/631,114; dated Dec. 18, 2019; United States Patent and Trademark Office; Alexandria, Virginia.

Justin N. Olamit; Office Action; U.S. Appl. No. 15/631,114; dated Jun. 3, 2019; United States Patent and Trademark Office; Alexandria, Virginia.

Justin N. Olamit; Office Action; U.S. Appl. No. 15/631,114; dated Jan. 17, 2019; United States Patent and Trademark Office; Alexandria, Virginia.

Justin N. Olamit; Notice of Allowance and Fees Due; U.S. Appl. No. 15/631,114; dated Apr. 9, 2020; United States Patent and Trademark Office; Alexandria, Virginia.

Justin N. Olamit; Corrected Notice of Allowability; U.S. Appl. No. 15/631,114; dated May 29, 2020; United States Patent and Trademark Office; Alexandria, Virginia.

Dirnberger, Johannes et al. Article Dated Jan. 2012; "Reproducibility for isometric and isokinetic maximum knee flexion and extension measurements using the IsoMed 2000 dynamometer"; Isokinetics and Exercise Science; pp. 149-153.

Gardiner, Gilbert Article Dated Nov. 22, 2016; "North Melbourne sports science invention set to take the sporting world by storm"; Herald Sun; North Melbourne, Australia.

Kangatechie (@kanga_tech); "Tweet Message"; Nov. 22, 2016; Tweet.

Sporttechie (@sporttechie); "Tweet Message"; Jun. 28, 2016; Tweet.

Wimpenny, Paul Article Dated Jul. 8, 2016; "Knee Flexion/Extension" ; Isokinetics.net.

Williams, Morgan (@Drmorgs); "Tweet Message"; Feb. 3, 2017; Tweet.

Screen capture of website as found on the Internet Archive Wayback Machine; Jun. 21, 2017; retrieved on Oct. 21, 2020 from <https://web.archive.org/web/20170621041335/http://valdperformance.com/groinbar-hip-strength-testing-system/.

Information pertaining to Public Disclosures set forth in the IDS Cover Letter submitted together with an Information Disclosure Statement on Dec. 15, 2020; 2 pages.

Order Granting Request for Ex Parte Reexamination dated Aug. 6, 2021; U.S. Reexamination No. 90/014,780 (SHE-REEXAM-100); United States Patent and Trademark Office; Alexandria, Virginia.

Exhibits Submitted with Request for Ex Parte Reexamination dated Jun. 21, 2021; U.S. Reexamination No. 90/014,780 (SHE-REEXAM-100); United States Patent and Trademark Office; Alexandria, Virginia.

Richard Wesorick; Reply by Third Party Requester In Ex Parte Re-examination of U.S. Pat. No. 10,729,369; US Re-examination No. U.S. Appl. No. 90/014,780; Dec. 6, 2021; United States Patent and Trademark Office; Alexandria, VA.

* cited by examiner

TESTING AND TRAINING APPARATUS

CROSS REFERENCE TO RELATED APPLICATION

This application is a continuation of U.S. patent application Ser. No. 15/631,114, filed Jun. 23, 2017, and entitled "TESTING AND TRAINING APPARATUS", the entire disclosure of which is hereby incorporated by reference herein.

FIELD OF THE INVENTION

The present invention relates generally to a testing and training apparatus, of particular but by no means exclusive application as an instrumented testing and training apparatus for measuring force produced through muscle contractions and exercising muscles with feedback, which may be portable and adjustable.

BACKGROUND OF THE INVENTION

Measuring the maximum voluntary contraction (MVC) of an isolated group of muscles provides valuable information regarding the ability of a user to perform and their propensity for injury. The MVC of an athlete can change frequently in response to training load, strength development and clinical and subclinical pathologies. Accordingly, regular measurement may be employed to identify injury risk. Existing methods of measuring MVC of isolated muscle groups, however, support only a very limited range of muscle groups, require significant setup time, or present the risk of injury when performing the testing.

One existing system is marketed as the Nordbord (trade mark) by Vald Performance Pty Ltd, while Biodex Medical Systems provides a number of trainers.

SUMMARY OF THE INVENTION

According to a first broad aspect of the present invention, there is provided a testing and training apparatus, comprising: an upright frame;
an instrumentation support that is supported by the upright frame so as to be adjustable in height; and
instrumentation mountable on the instrumentation support;
wherein the instrumentation comprises a plurality of force sensors, and is rotatable relative to the upright frame; and
the apparatus is controllable to output data signals indicative of force detected by the force sensors.

It will be appreciated that the upright frame, though generally 'upright', may be inclined in whole or part from the vertical, even to a great extent, provided that it nonetheless allows the instrumentation to be changed in height as the instrumentation support is moved on or relative to the upright frame.

Also, it should be appreciated that the instrumentation support need not be integral, but may comprise a plurality of components, each supported by the upright frame and adjustable in height on the upright frame. This may be especially applicable in embodiments in which the instrumentation is distributed.

In an embodiment, the instrumentation comprises a control panel, a plurality of load cells, a battery, a microcontroller and a data communication bus.

In another embodiment, the instrumentation is distributed, each of the force sensors comprising a control panel, a load cell, a battery, a microcontroller and a data communication bus.

In certain embodiments, the instrumentation comprises a plurality of LED or other indicators corresponding to the respective force sensors, wherein the indicators are activatable to identify to a user which of the force sensors to employ.

The instrumentation support may comprise a horizontal member and/or a plurality of brackets or sleeves adjustable in position on the upright frame.

The instrumentation may be controllable to selectively activate one or more of the force sensors according to a desired testing or training exercise. In one example, the instrumentation is controllable with controls provided therein. In another example, the instrumentation is controllable with a computing device when in data communication with the instrumentation; the computing device may be external, or the apparatus may further comprise the computing device.

In some embodiments, the apparatus further comprises a portable base.

In certain embodiments, the instrumentation is rotatable about a horizontal axis.

In a further embodiment, the apparatus further comprises folding hinged mounts for supporting the upright frame.

In some embodiments, the apparatus is configured to facilitate isometric exercise (whether for testing or training).

According to a second broad aspect of the present invention, there is provided a testing or training method, comprising:
locating instrumentation with an instrumentation support on an upright frame at a height and with a rotational orientation selected according to a desired testing or training exercise, the instrumentation comprising a plurality of force sensors;
conducting the testing or training exercise; and
outputting data signals indicative of force detected by the force sensors;
wherein the instrumentation is rotatable relative to the upright frame.

In one embodiment, the method comprises adjusting the rotational orientation of the instrumentation during or between exercises (such as of an exercise protocol).

Thus, the present invention provides, in certain embodiments, an instrumented, portable and adjustable testing and training apparatus that supports, for example, measurement of maximum voluntary contraction and/or training. Various embodiments facilitate measurement and/or training in plural planes, through an adjustable frame with rotatable bar which can be quickly set up to isolate specific muscle groups.

It should be noted that any of the various individual features of the above aspects of the invention, and any of the various individual features of the embodiments described herein including in the claims, can be combined as suitable and desired when technically feasible.

BRIEF DESCRIPTION OF THE DRAWING

In order that the invention may be more clearly ascertained, embodiments will now be described, by way of example, with reference to the accompanying drawing, in which.

DETAILED DESCRIPTION OF EMBODIMENTS

It will be appreciated that all illustrations of the drawings are for the purpose of describing selected embodiments of the present invention and are not intended to limit the scope of the present invention.

Figure 1:
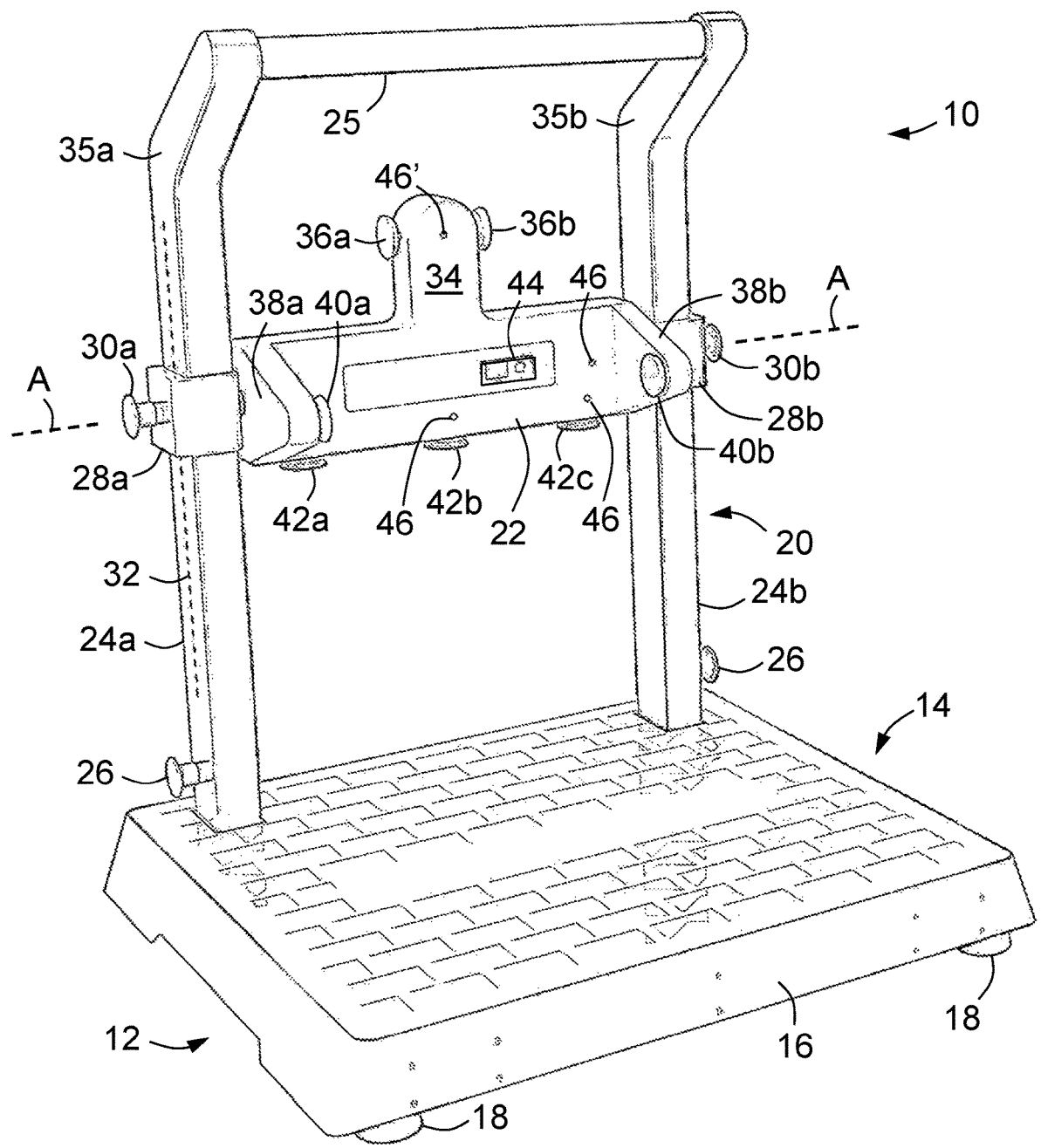
FIG. 1 is a front view of an instrumented strength testing and training apparatus according to a first embodiment of the present invention.

FIG. 1 is a perspective view of an instrumented strength testing and training apparatus 10 according to an embodiment of the present invention. Apparatus 10, which is generally portable, includes a sturdy base 12 with a removable top panel 14, a skirt 16 (which protects other elements of base 12), stabilising feet 18 (of which two of typically four are shown in this view) and, optionally, wheels not shown) attached to skirt 16 at its rear in this view (and hence not visible in this figure). Stabilising feet 18 are preferably adjustable, and provide a stable support for base 12 on uneven flooring.

Apparatus 10 includes a upright frame 20 and instrumentation in the form, in this embodiment, of an instrument unit 22. Instrument unit 22 is supported by and between upright members 24a, 24b of upright frame 20. Upright frame 20 also includes a handle 25 that joins upright members 24a, 24b at their upper ends. Handle 25 provides bracing strength to upright frame 20 and is also used as a handle by the user when changing position. Furthermore, handle 25 may be used as a mounting location for a tablet computer. In the alternative embodiment (cf. FIG. 13), upright members 24a, 24b and handle 25 are attached to each other (either integrally or detachably) using curved corners.

Upright members 24 are detachably attached to base 12, as is described below; this detachable attachment is facilitated by locking pins 26, which may be spring loaded, that pass through respective upright members 24a, 24b and engage mounts (not shown) of base 12. These mounts (cf. FIGS. 6A and 6B) are preferably rotatably mounted to base 12, and extend sufficiently through top panel 14 (when rotated to an upright orientation) to allow upright members 24a, 24b to be located on these mounts, and held in place with locking pins 26. When partially withdrawn from upright members 24a, 24b, locking pins 26 disengage these mounts and allow upright frame 20 to be removed.

In an alternative arrangement, upright members 24a, 24b may be detachably attached to fixed floor mounts located below base 12.

Instrument unit 22 is of a generally inverted (in its basic configuration) "T" shape, but is rotatably mounted to sleeves 28a, 28b in turn supported by upright members 24a, 24b. Sleeves 28a, 28b are slidably adjustable in position along upright members 24a, 24b, and may be locked at a desired position with respective sprung height locking pins 30a, 30b that are received by locating holes 32 in the outer surfaces of upright members 24a, 24b. In use, therefore, instrument unit 22 is rotatable about a rotational axis A (which in this example is horizontal). This allows force applied to force sensors of instrument unit 22 to be applied at many angles while remaining perpendicular to at least some of the force sensors. Instrument unit 22 may be raised and lowered on upright frame 20. The sprung height locking pins 30a, 30b can be disengaged by the user by pulling them out, allowing instrument unit 22 to slide on sleeves 28a, 28b. When the desired height is reached, the user can engage locking pins 26 into locating holes 32 in upright members 24a, 24b; locating holes 32 allow locking pins 26 to fix instrument unit 22 in position. Instrument unit 22 may alternatively be fixed in position with a rack and pinion system to allow continuous adjustment (see, for example, FIG. 14). Alternatively, a motorised rack and pinion system may be used to allow automated adjustment of the height of instrument unit 22.

In this embodiment, upright members 24a, 24b include respective bends 35a, 35b that locate handle 25 towards the front (as shown in FIG. 1) of apparatus 10, allowing stem 34 of instrument unit 22 to avoid handle 25 when instrument unit 22 is raised and thus allow instrument unit 22 to be raised higher than would otherwise be possible. Bends 35a, 35b may also position handle 25 in a more convenient position for the user. Bends 35a, 35b also allow the user's body to move within upright frame 20 while performing certain exercises.

Instrument unit 22 includes a plurality of force sensors. Located on the sides of stem 34 of the "T" are force sensors 36a, 36b, oriented outwards to measure horizontal force directed inwardly towards the stem 34. Force sensors 30a, 30b are thus used for measuring force applied parallel to the rotational axis A of instrument unit 22 and towards the centre line of upright frame 20, that is, towards each other.

Instrument unit 22 also includes forwardly extending side wings 38a, 38b, on the inner faces of which are located force sensors 40a, 40b, oriented towards each other to receive force directed horizontally away from centre line of upright frame 20 and thus away from each other. Thus, force sensors 40a, 40b are used for measuring force applied parallel to rotational axis A of instrument unit 22 and towards the outside of upright frame 20.

The lower surface of instrument unit 22 is provided with a plurality of force sensors 42a, 42b, 42c (in this example, three) for measuring force applied perpendicular to the rotational axis A of instrument unit 22. Measuring force in this axis allows unilateral and bilateral testing of many specific muscle groups Instrument unit 22 is also provided with a control panel 44 for controlling instrument unit 22, and illuminating indicators 46 (such as LEDs) that are illuminated by controlling software (described below) to indicate to the user which of the force sensors are to be used in the instant exercise. (Note that force sensors 36a, 36b on the stem 34 of instrument unit 22 may share a single indicator 46' in this example.)

In this embodiment, control panel 44 include a push button to control power to apparatus 10, and a display (such as an LCD display) that, in use, indicates whether a data connection with an associated computing device (not shown) is active. Indicators 46 are used to show the user which force sensors are to be active during a specific exercise. Alternatively, indicators 46 may be omitted and the display may be configured to show the user which force sensors are to be active and employed. Optionally, apparatus 10 may include a vibrating mechanism to provide haptic feedback to the user.

Figure 2:
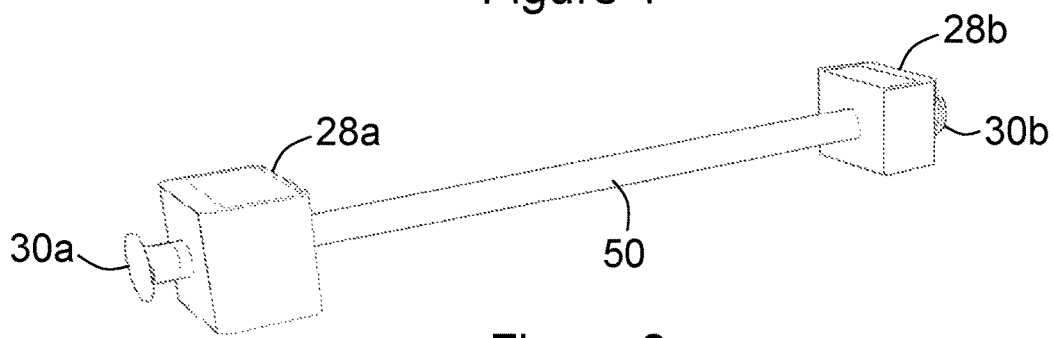
FIG. 2 is a front view of an instrument unit support of the apparatus of FIG. 1.

FIG. 2 is a front view of an instrument unit support of apparatus 10 in the form of a horizontal member or bar 50, for supporting instrument unit 22. Horizontal bar 50, in this example, is attached to and couples sleeves 28a, 28b to one another. Instrument unit 22 is pivotable about horizontal bar 50.

Horizontal bar 50, in this example, is integral, but may alternatively comprise two separate segments each pivotably coupled to instrument unit 22. In that case, horizontal bar 50 does not couple sleeves 28a, 28b to one another; this is done by the combination of horizontal bar 50 and instrument unit 22.

Figure 3A:
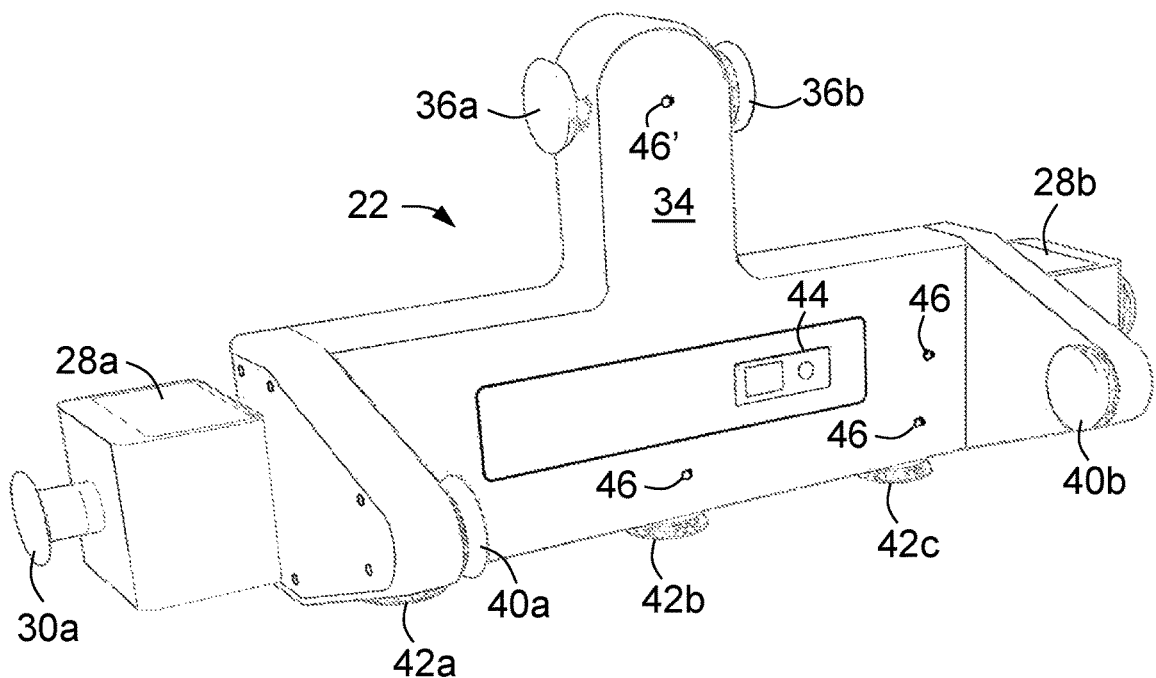
FIG. 3A is a front view of the instrument unit of the apparatus of FIG. 1, detached from the adjustable frame, also showing the sleeves and locking pins of the apparatus.
Figure 3B:
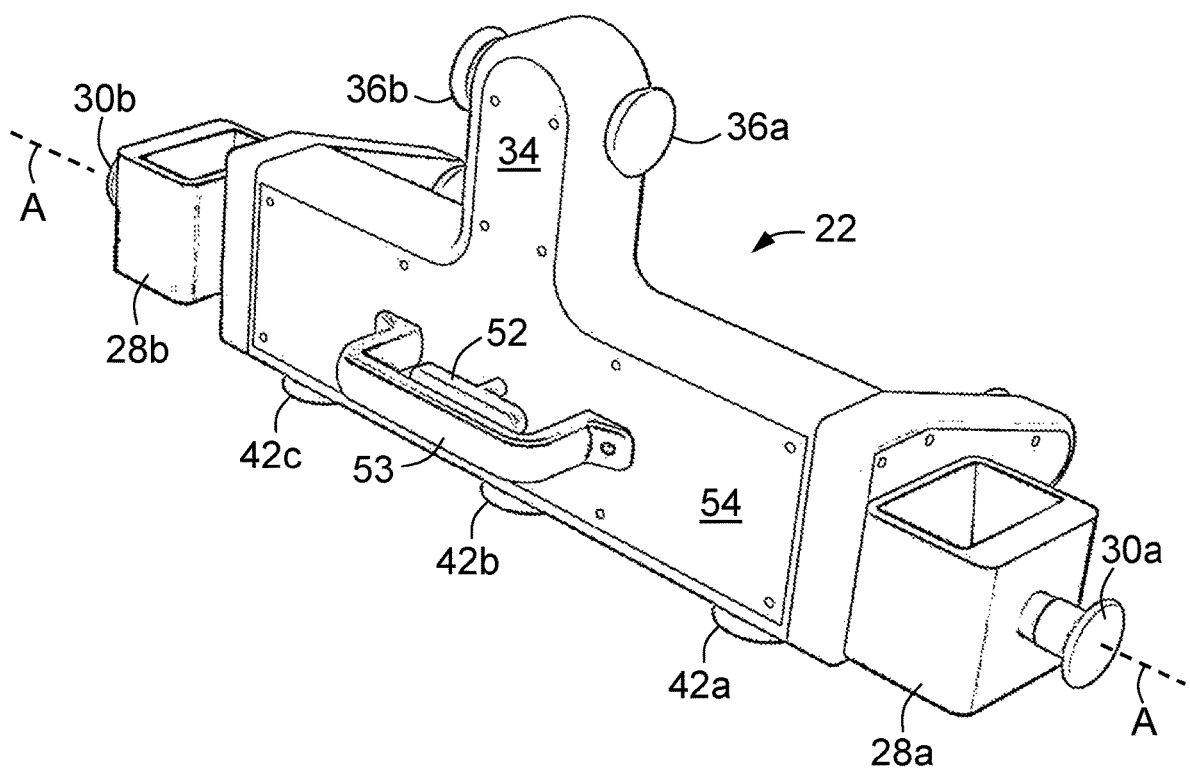
FIG. 3B is a rear view of the instrument unit of the apparatus of FIG. 1, detached from the adjustable frame, also showing the sleeves and locking pins of the apparatus.

FIGS. 3A and 3B are corresponding front and rear views of instrument unit 22 of apparatus 10 of FIG. 1 (shown detached from upright frame 20). Referring to FIG. 3B, instrument unit 22 includes a locking pin 52 that frictionally engages or locates within blind bores in horizontal bar 50, and a handle 53 attached to a removable rear access panel 54 of instrument unit 22. Locking pin 52, when engaged, prevents instrument unit 22 from rotating around horizontal bar 50.

By squeezing locking pin 52 and handle 53 together, a user can disengage locking pin 52 from horizontal bar 50, and then manipulate handle 53 to rotate instrument unit 22 about horizontal bar 50 to a desired rotational orientation. The user then releases locking pin 52 to fix instrument unit 22 at the desired rotational orientation.

In an alternative embodiment (cf. FIG. 15), the rotational orientation could be locked using a screw tightening mechanism.

Figure 4:
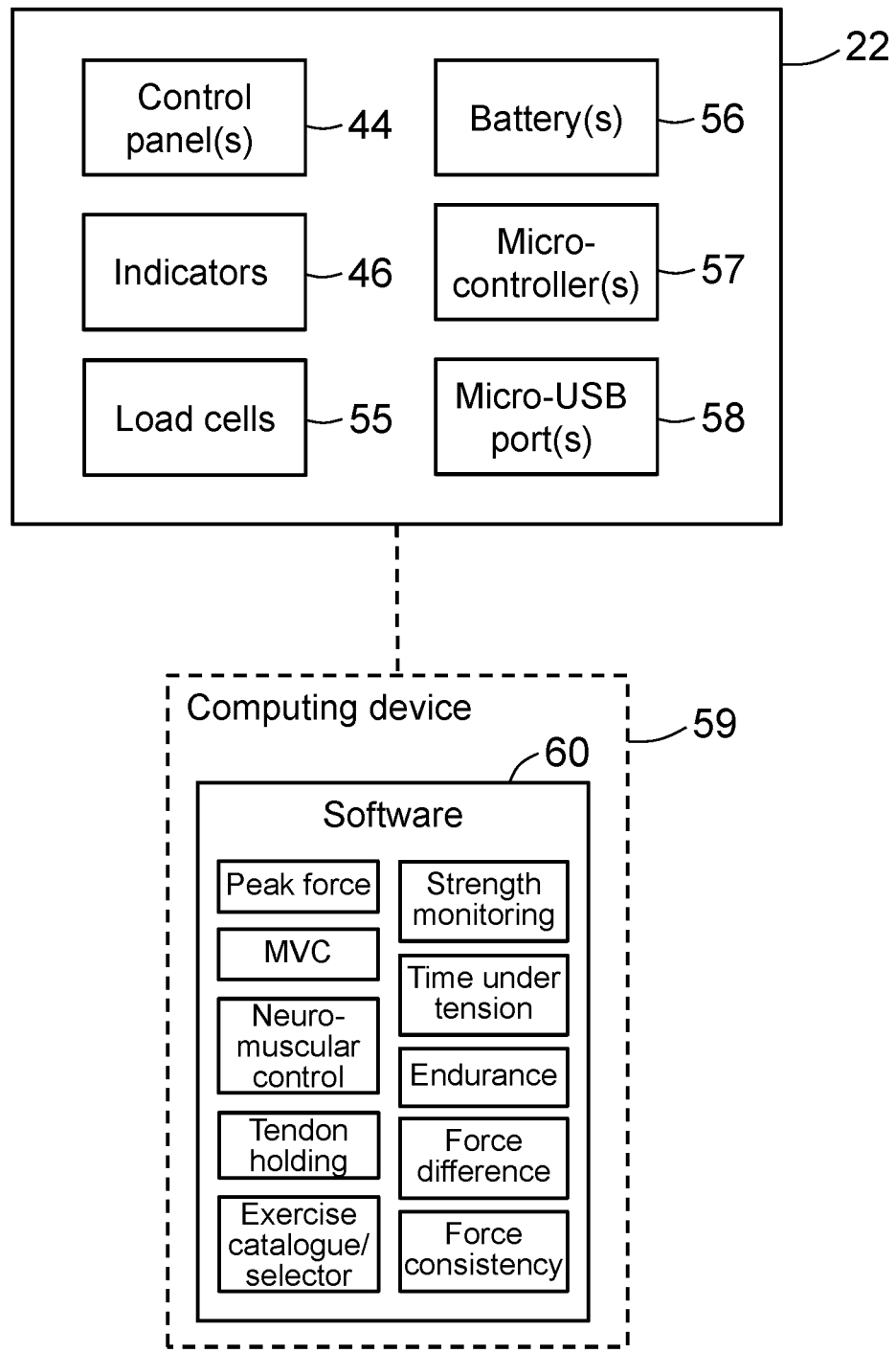
FIG. 4 is a schematic view of the instrument unit of the apparatus of FIG. 1.

FIG. 4 is a schematic view of instrument unit 22 of apparatus 10 of FIG. 1. Instrument unit 22 includes (in addition to control panel 44 and indicators 46) a plurality of load cells 55, a rechargeable battery 56, a microcontroller 57 (with and associated circuitry), and a data bus in the form of a micro-USB port or the like 58. Microcontroller 57 (with associated circuitry) process analogue signals from each of load cell 55 and transmits a series of timestamped measurements of instantaneous force to an associated, computing device 59 (such as a laptop or desktop computer, or a tablet or smartphone) via a wired or wireless interface. In this embodiment, computing device 59 external is external to apparatus 10, that is, is not a part of apparatus 10, but in other embodiments apparatus 10 may include computing device 59.

Micro-USB port or the like 58 is used to charge battery 56, and acts as a wired interface in pertinent embodiments. The wireless connection may employ a known radio frequency protocol such as Bluetooth™.

Computing device 59 is provided with software 60 that supports the real-time display of the measured forces, providing real-time feedback to the user. Software 60 also calculates the peak force produced over a specified time period, which may then be stored as the user's MVC. Software 60 may also guide the user through an exercising session, by displaying a target force on the screen alongside the force being produced. Thus, the user may be provided with real-time feedback on the quality of a muscle contraction, measured—for example—according to the difference between the produced force and the target force, and/or the consistency of the force (e.g. in direction and/or magnitude) over a specified time period.

For this purpose, software 60 includes measurement modules for measuring and determining various parameters, including peak force, MVC, neuro-muscular control, tendon holding, strength, time under tension, endurance, force difference (i.e. between produced force and target force), and force consistency.

In this embodiment, software 60 also includes a catalogue of selectable exercise protocols or regimes, including instructions for how they should be performed. When the user selects a particular exercise with software 60, software 60 controls instrument unit 22 to illuminate one or more of indicators 46 to identify to the user which of the force sensors should be used in that exercise. For example, in a bilateral supine hip adduction exercise, indicator 46' (cf. FIG. 3A) is illuminated to indicate that force sensors 36a and 36b should be used.

It will be appreciated that, while in this embodiment computing device 59 with software 60 is external to apparatus 10, in other embodiments apparatus 10 may include the computing device. In an example of such an embodiment, the computing device is incorporated in instrument unit 22.

Figure 5:
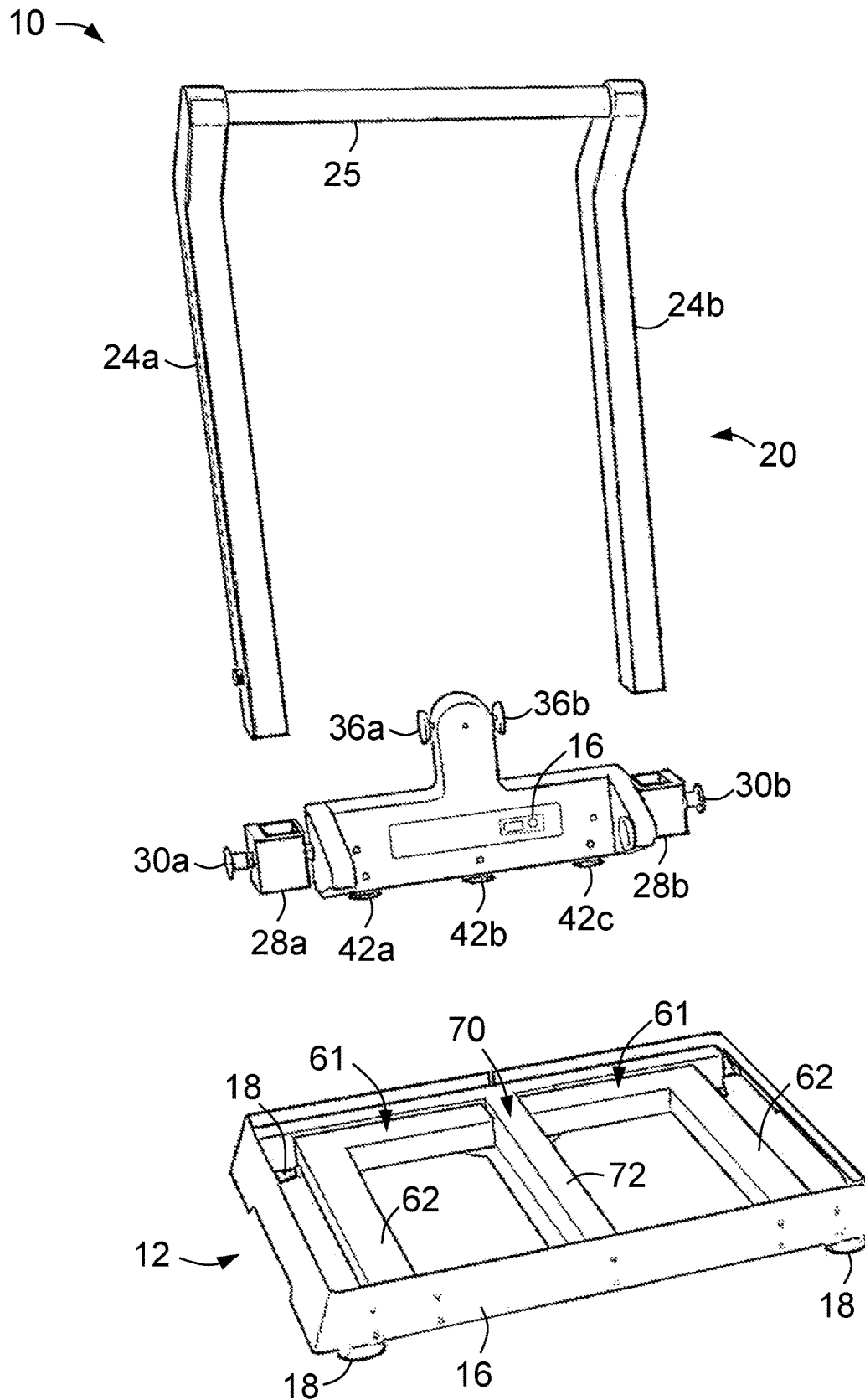
FIG. 5 is an exploded partial view of the apparatus of FIG. 1, showing the mounts of the base folded and the top panel removed.
Figure 6A:
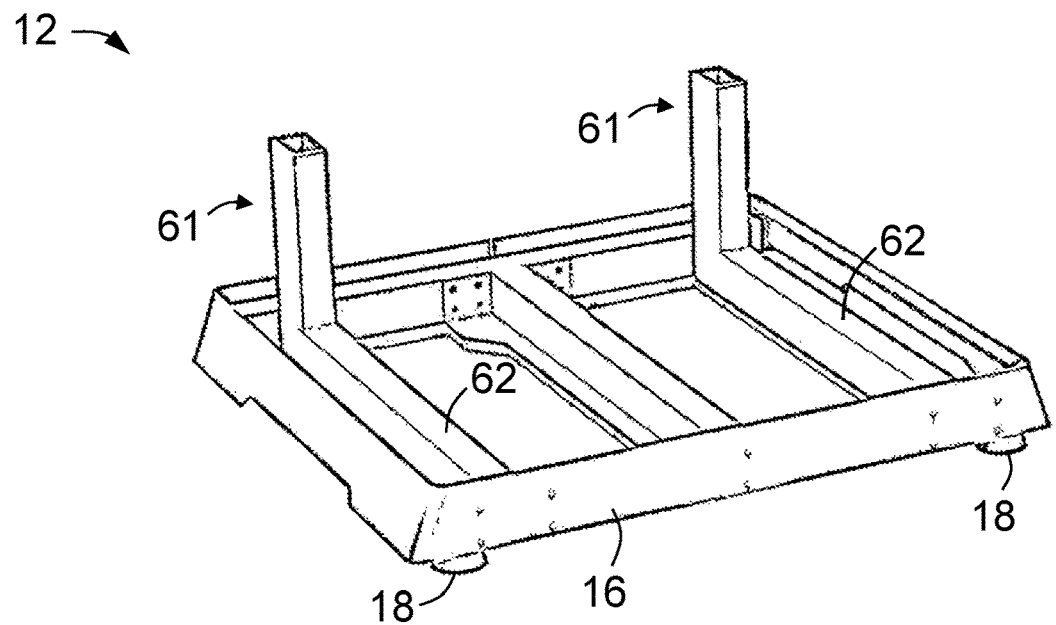
FIG. 6A is a view of the base of the apparatus of FIG. 1, with the mounts of the base unfolded and the top panel removed.
Figure 6B:
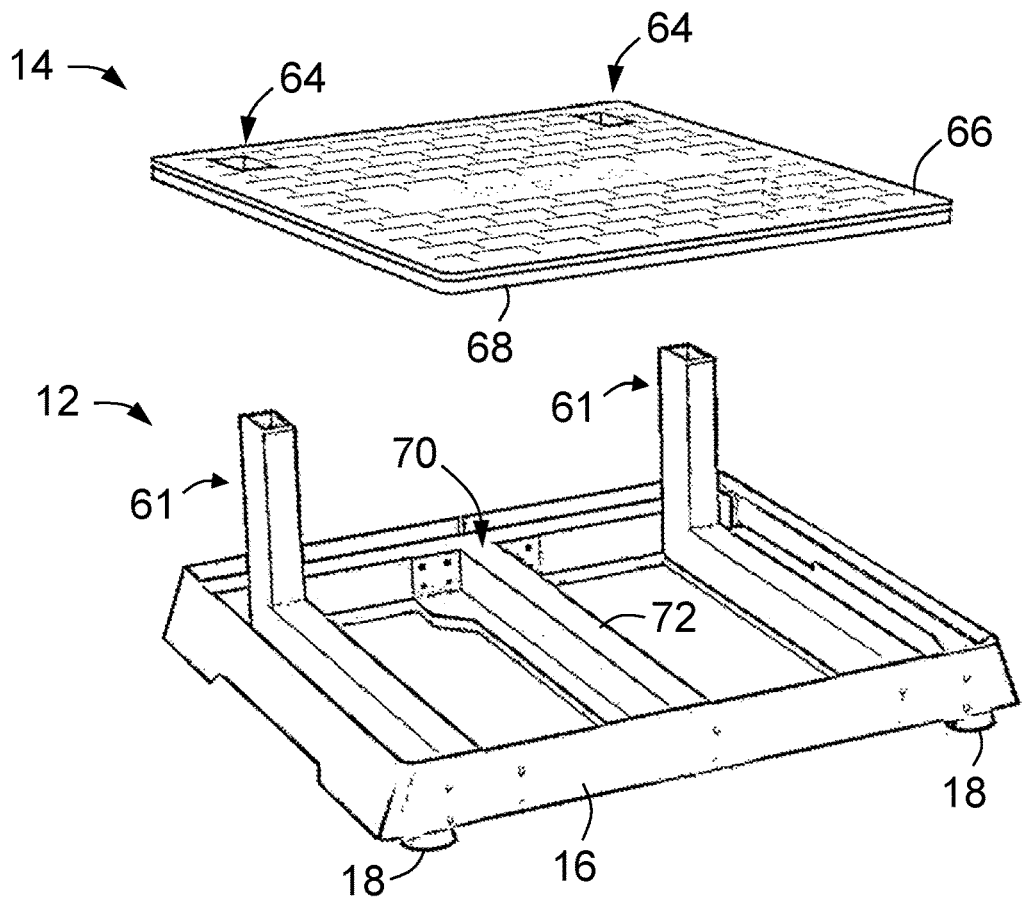
FIG. 6B is a view of the base of the apparatus of FIG. 1, showing how its top panel locates on the base.

FIGS. 5 to 6B illustrate the assembly of base 12 to upright frame 20. FIG. 5 is an exploded partial view of apparatus 10, showing mounts 61 of base 12 folded flat into base 12 and top panel 14 removed. Mounts 61 may be rotatably attached to the rest of base 12 by any convenient mechanism, such as with hinges or pairs of pins. Mounts 61 thus may be folded down into base 12, as shown, for convenience of transportation. Mounts 61 are, in this embodiment, "L" shaped so, when rotated, each mount 61 typically rotates about the base 62 of the "L" or about a hinge attached thereto.

FIG. 6A is a view of base 12 of apparatus 10, with mounts 61 of base 12 unfolded and top panel 14 again removed. In this upright orientation, mounts 61 allow upright frame 20 to be attached thereto. In an alternative embodiment, however, mounts 61 may be fixed to base 12 and neither fold nor unfold. Still alternatively, upright frame 20 may be permanently fixed to base 12, that is, not removable, but this may be less convenient in some applications.

FIG. 6B is a view of base 12 of apparatus 10, showing how its top panel 14 locates on base 12. Top panel 14 includes holes 64 that, when base 12 is assembled and mounts 61 are upright, coincide with mounts 61 so that mounts 61 can extend upwardly through holes 64. Top panel 14 has two layers: an upper layer 66 of a resilient material for the comfort of the user, such as of high density foam, rubber or carpet (which may be textured to increase grip), and a rigid lower layer 68 to give top panel 14 sufficient strength to support a user. Upper and lower layers 66, 68 are fastened together by any suitable mechanism; they may be permanently fastened to one another (such as with glue or staples) or detachably fastened to one another (such as with Velcro™) so that upper layer 66 can be readily detached for cleaning or replacement.

Also shown in this view is an "H" shaped internal frame 70 of base 12 (including a support brace 72, providing the bar of the "H"), which supports skirt 16, mounts 61, feet 18 and top panel 14 when in situ. Thus, in use, internal frame 70 and bases 62 of mounts 61 support top panel 14 and hence the user, while internal frame 70 and mounts 61 stabilize upright frame 20 as force is applied to the various force sensors of instrument unit 22.

Figure 7:
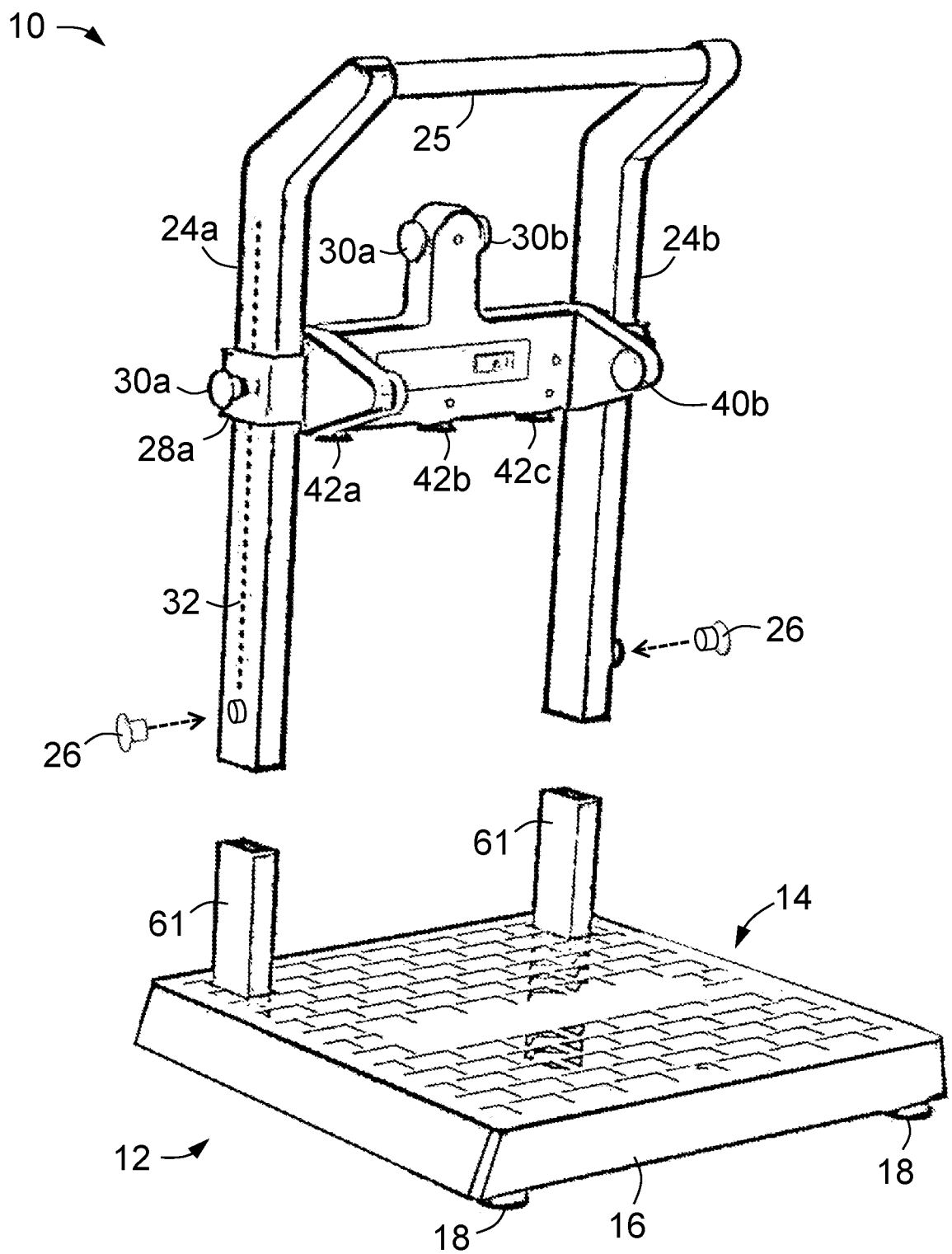
FIG. 7 is a front view of the apparatus of FIG. 1, showing how the upright frame locates into the base.

FIG. 7 is a front view of apparatus 10, showing how upright frame 20 locates onto mounts 61 and hence to base 12. To assemble apparatus 10, upright members 24a, 24b of upright frame 20 are positioned about and receive mounts 61, then upright frame 20 is slit downwardly until maximally engaged. Locking pins 26 are then tightened to secure upright members 24a, 24b to mounts 61.

Figure 8:
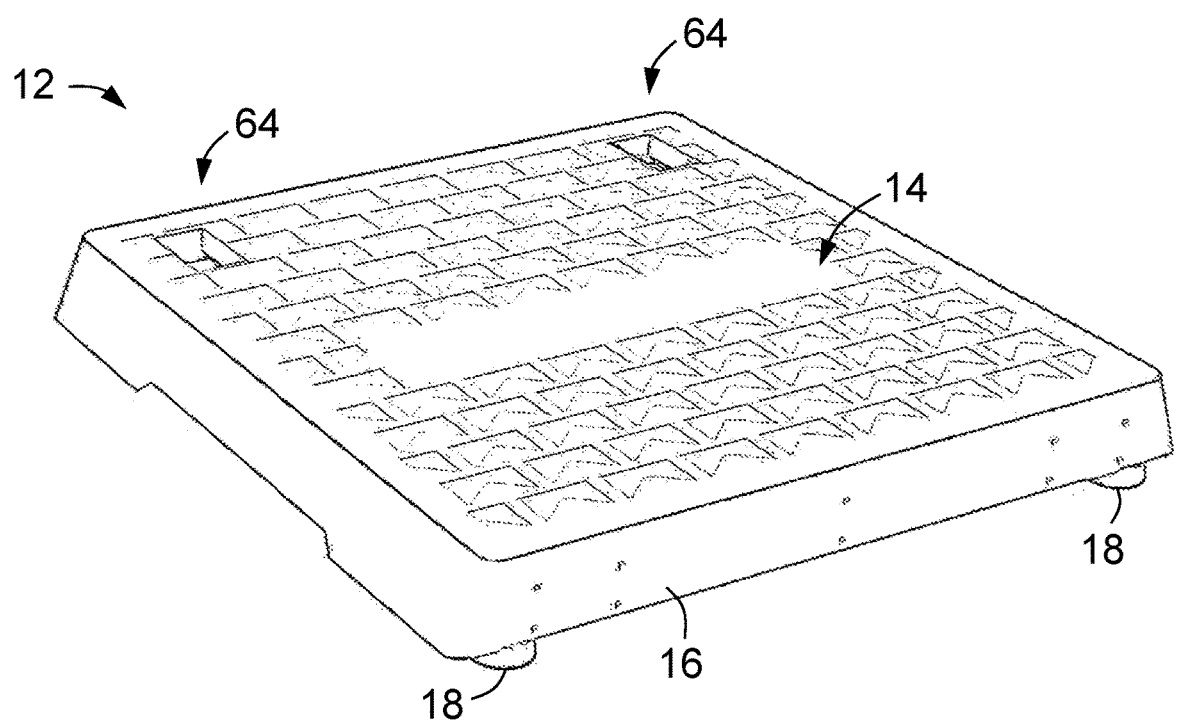
FIG. 8 is a front view of the base of the apparatus of FIG. 1, wherein the mounts are folded down and the top panel is inserted.

FIG. 8 is a front view of base 12 of apparatus 10, with mounts 61 are folded down and top panel 14 inserted. Hence, mounts 61 are not visible in this view, concealed by top panel 14.

Figure 9:
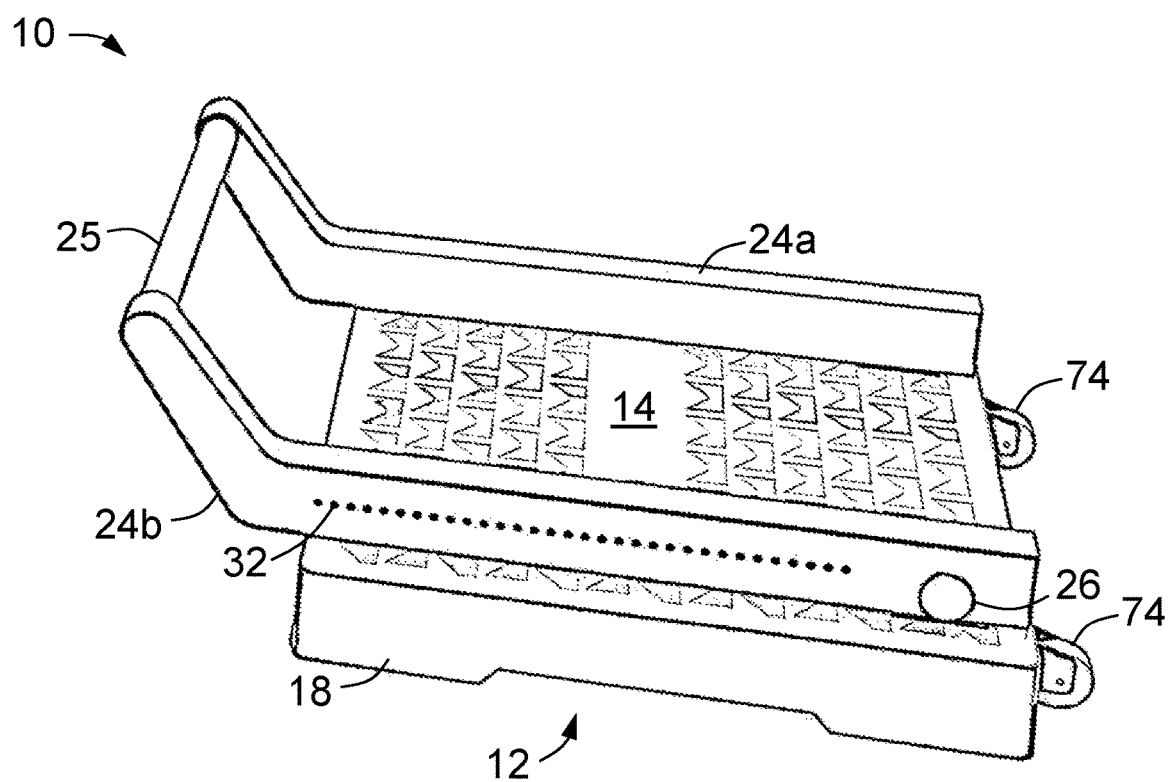
FIG. 9 is a right view of the apparatus of FIG. 1, wherein the upright frame is detached, the instrument panel is removed and the present invention is ready for transportation.

FIG. 9 is a right view of apparatus 10 of FIG. 1, with upright frame 20 detached but placed on base 12 and instrument unit 22 removed, so that apparatus 10 is ready for transportation. Wheels 74 of base 12 are also shown in this view, which may be used to roll apparatus 10 when it is being transported (especially while assembled).

Figure 10:
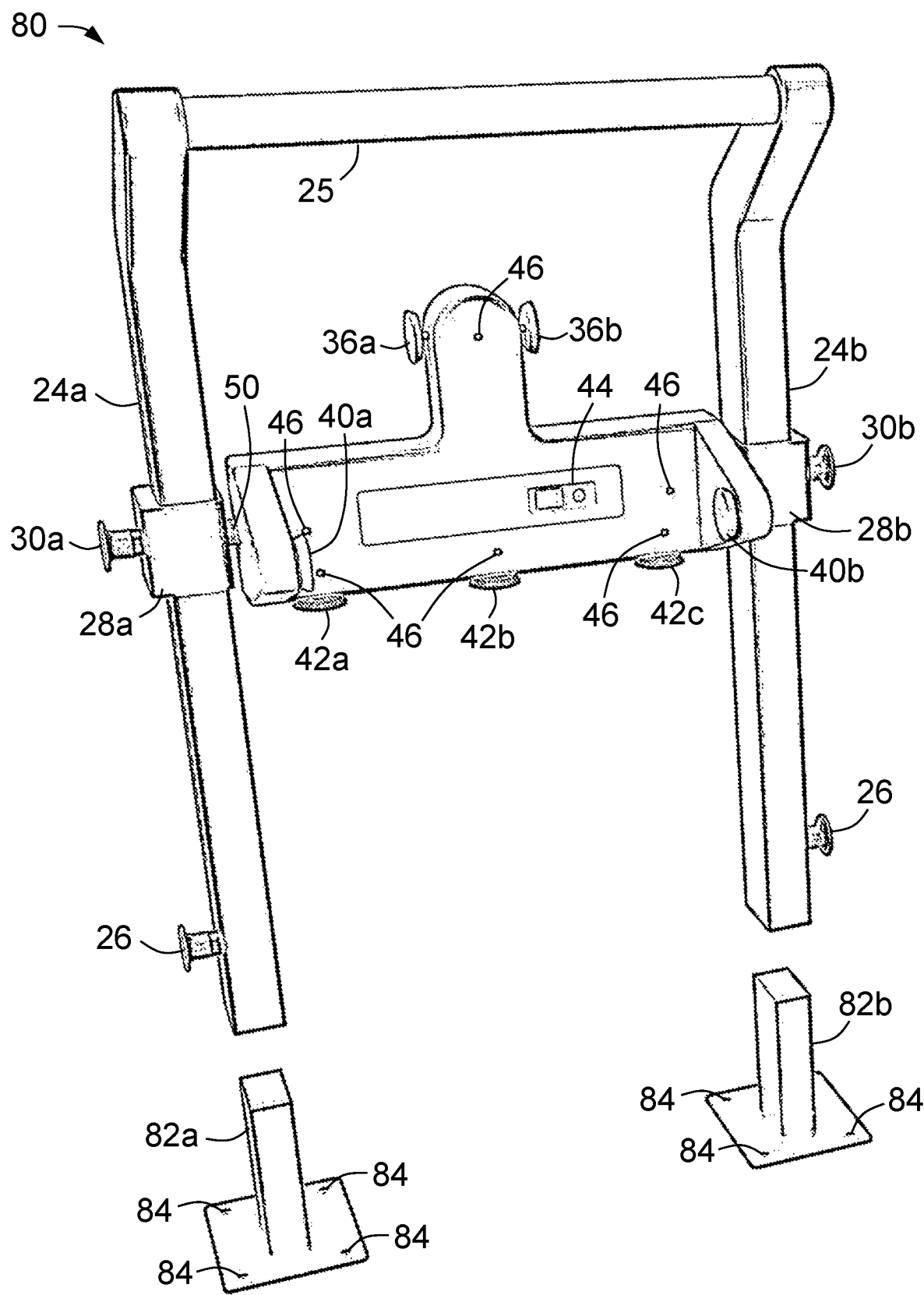
FIG. 10 is a front view of an instrumented strength testing and training apparatus according to a second embodiment of the present invention, with its upright frame shown detached from its floor mounts.

FIG. 10 is a front view of an instrumented strength testing and training apparatus 80 according to a second embodiment of the present invention. Apparatus 80 is similar in many respect to apparatus 10 of FIG. 1, and like reference numerals have been used to identify like features. However, rather than having a free-standing base (cf. base 12 of apparatus 10 of FIG. 1), apparatus 80 is configured to be detachably mounted to a floor or other supporting surface. To this end, apparatus 80 includes mounts 82a, 82b for detachably supporting upright members 24a, 24b, respectively. Mounts 82a, 82b may be compared to mounts 61 of apparatus 10 of FIG. 1, but are adapted to be attached using bolts, screws, rivets or the like to a floor or other supporting surface. Consequently, mounts 82a, 82b are provided with holes 84 for receiving, for example, such bolts or screws. In FIG. 9, upright frame 20 is shown detached from mounts 82a, 82b.

Thus, when installing apparatus 80, mounts 82a, 82b may be attached securely to, for example, a floor using holes 84 and bolts or the like. Upright frame 20 may then be fitted onto mounts 82a, 82b and locked in place using locking pins 26. In this setup, apparatus 80 is stable and requires less space than with the portable base 12 of apparatus 10 of FIG. 1, but is correspondingly more difficult to relocate.

FIG. 1 illustrates apparatus 10 in only one configuration for its use: with instrument unit 22 arranged in an upright orientation. As noted above, however, instrument unit 22 may be rotated about rotational axis A and secured at essentially any desired rotational angle, according to—for example—the direction of the force it is desired to measure with force sensors 42a, 42b, 42c, or which of force sensors 36a, 36b or force sensors 40a, 40b are desirably to be most readily accessed. Thus, FIG. 11 illustrates another exemplary configuration, in which instrument unit 22 is arranged generally downwardly, that is, with stem 34 of instrument unit 22 rotated forwardly (relative to the configuration shown in FIG. 1) by about 170 degrees.

Figure 11:
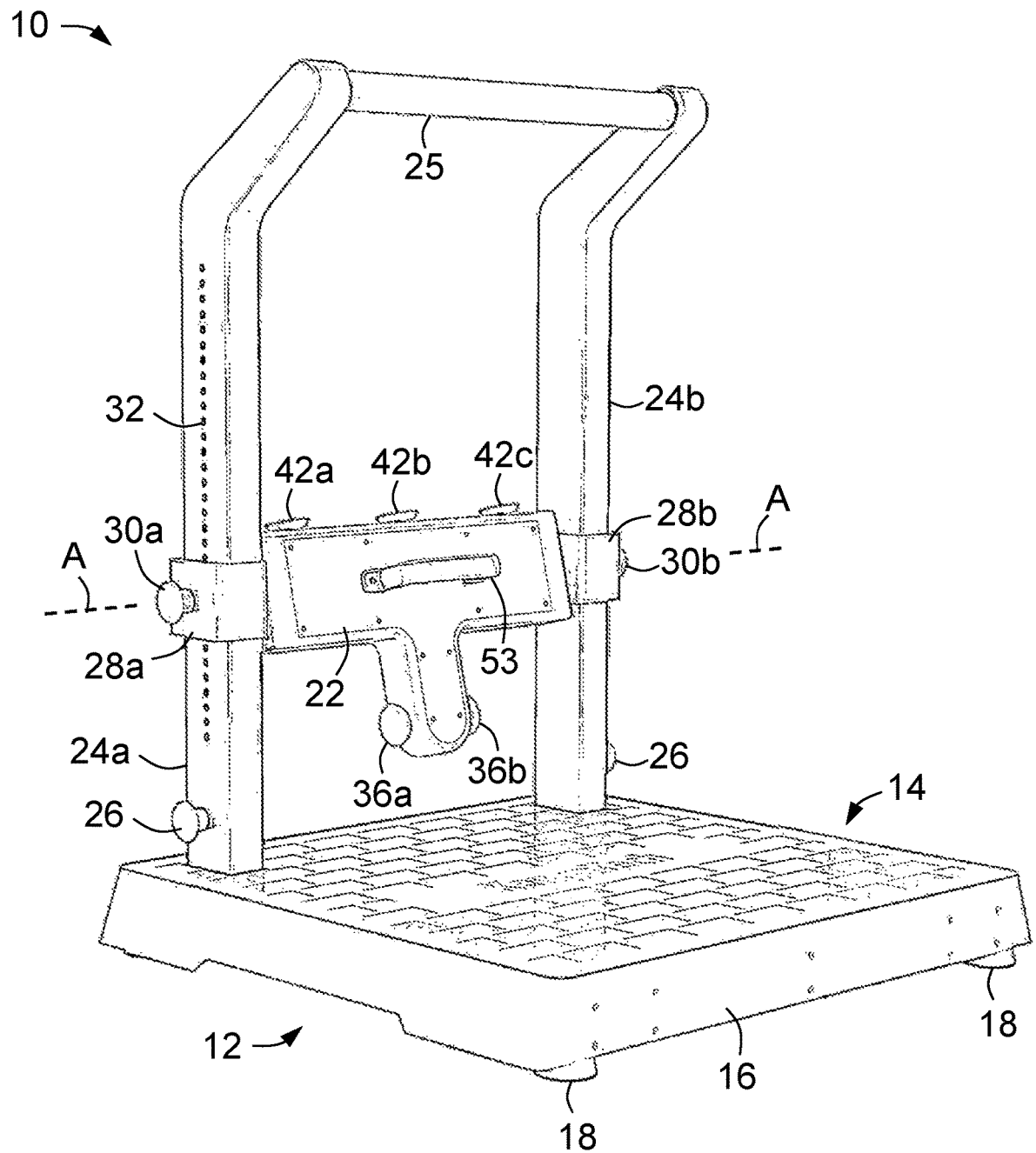
FIG. 11 is a front view of the apparatus of FIG. 1, with the instrument unit rotated to measure inwardly opposed forces.

In the configuration of FIG. 11, force sensors 36a, 36b located on stem 34 are usable for, in general, different testing protocols. For example, this configuration may be used in a number of specific protocols, including measuring force during bilateral supine hip adduction where applying the force in opposing directions allows a user to self-stabilise.

As discussed above, force sensors 36a, 36b measure force applied parallel to rotational axis A of instrument unit 22 and towards the centre line of upright frame 20 and thus towards each other. With reference to FIG. 11, force sensors 36a, 36b can be used when instrument unit 22 is oriented as depicted in this figure.

Force sensors 42a, 42b, 42c are used for measuring force applied perpendicular to rotational axis A of instrument unit 22. With reference to FIG. 11, force sensors 42a, 42b, 42c can be used when instrument unit 22 is arranged as shown, such that force sensors 42a, 42b, 42c can be readily used to measure force directed generally downwards, but instrument unit 22 can be rotated so that the force can be applied at essentially any angle, which allows the user to ensure that the force is being applied perpendicularly to the testing lever, for example the user's arm or leg. Measuring force in this axis allows unilateral and bilateral testing of many specific muscle groups.

Figure 12:
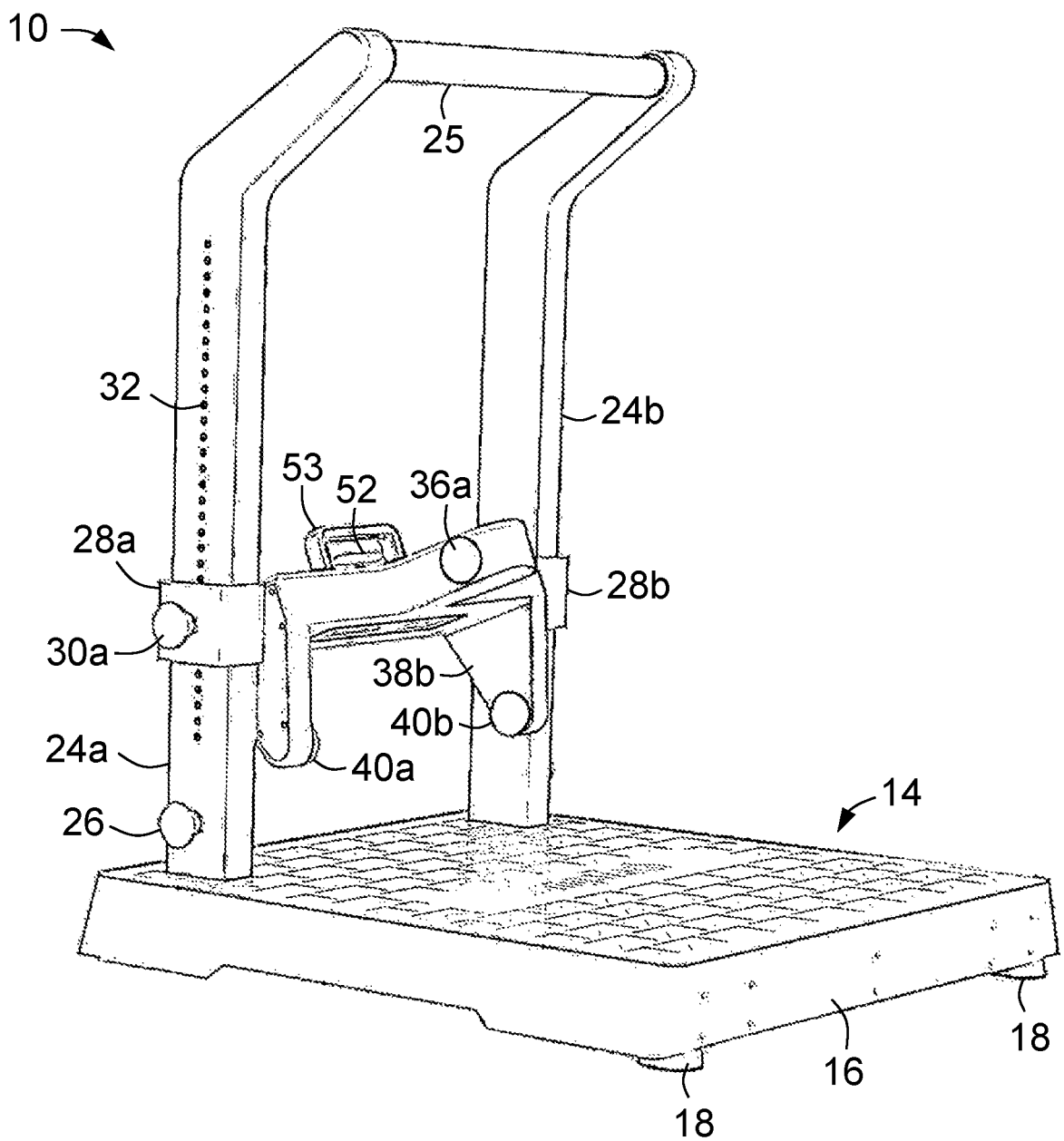
FIG. 12 is a front view of the apparatus of FIG. 1, with the instrument unit rotated to measure outwardly opposed forces.

FIG. 12 is a front view of apparatus 10 of FIG. 1, with instrument unit 22 rotated forward (compared with the configuration shown in FIG. 1) by about 70 degrees, to support outwardly opposed forces with force sensors 40a, 40b. Thus, when instrument unit 22 is arranged in this configuration, force sensors 40a, 40b can be readily used. Force is measured in this axis with force sensors 40a, 40b in a number of specific protocols, including bilateral hip abduction. As with sensors 36a, 36b on stem 34 of instrument unit 22, performing the protocol bilaterally allows the user to self-stabilise by applying a balancing force in each direction.

Figure 13:
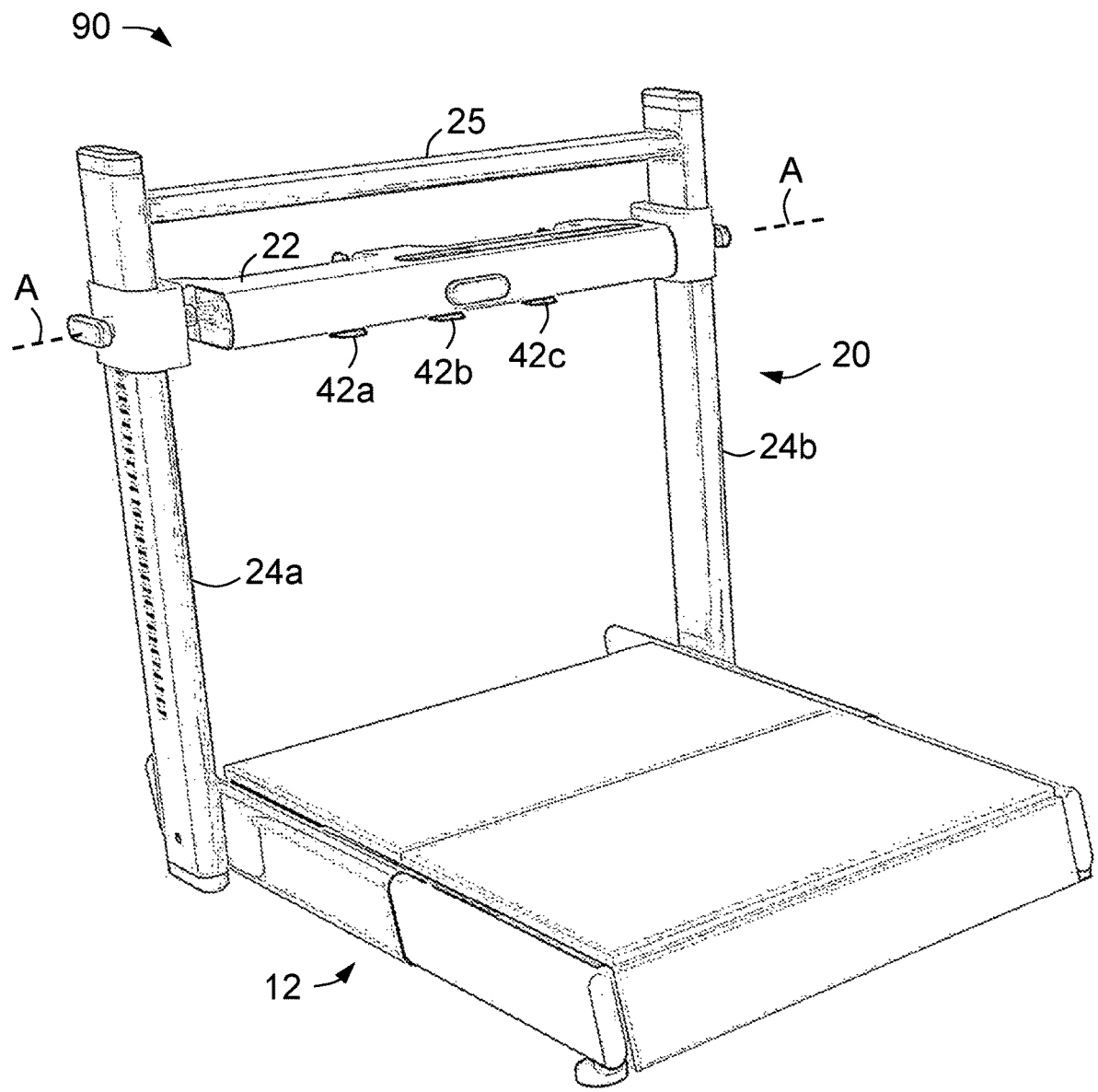
FIG. 13 is a front perspective view of an instrumented strength testing and training apparatus according to a first alternative embodiment of the invention.
Figure 14:
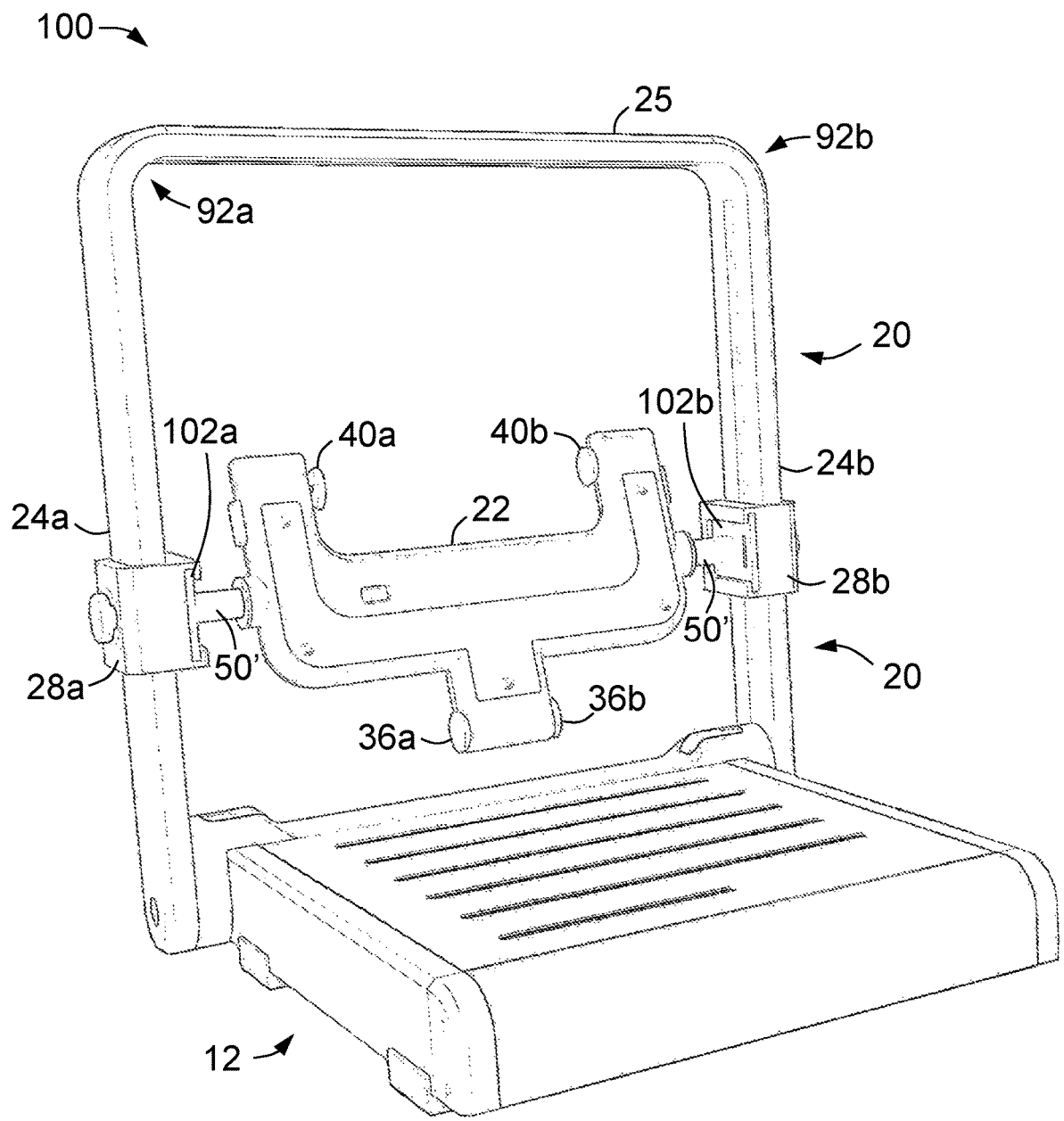
FIG. 14 is a front perspective view of an instrumented strength testing and training apparatus according to a second alternative embodiment of the invention.
Figure 15:
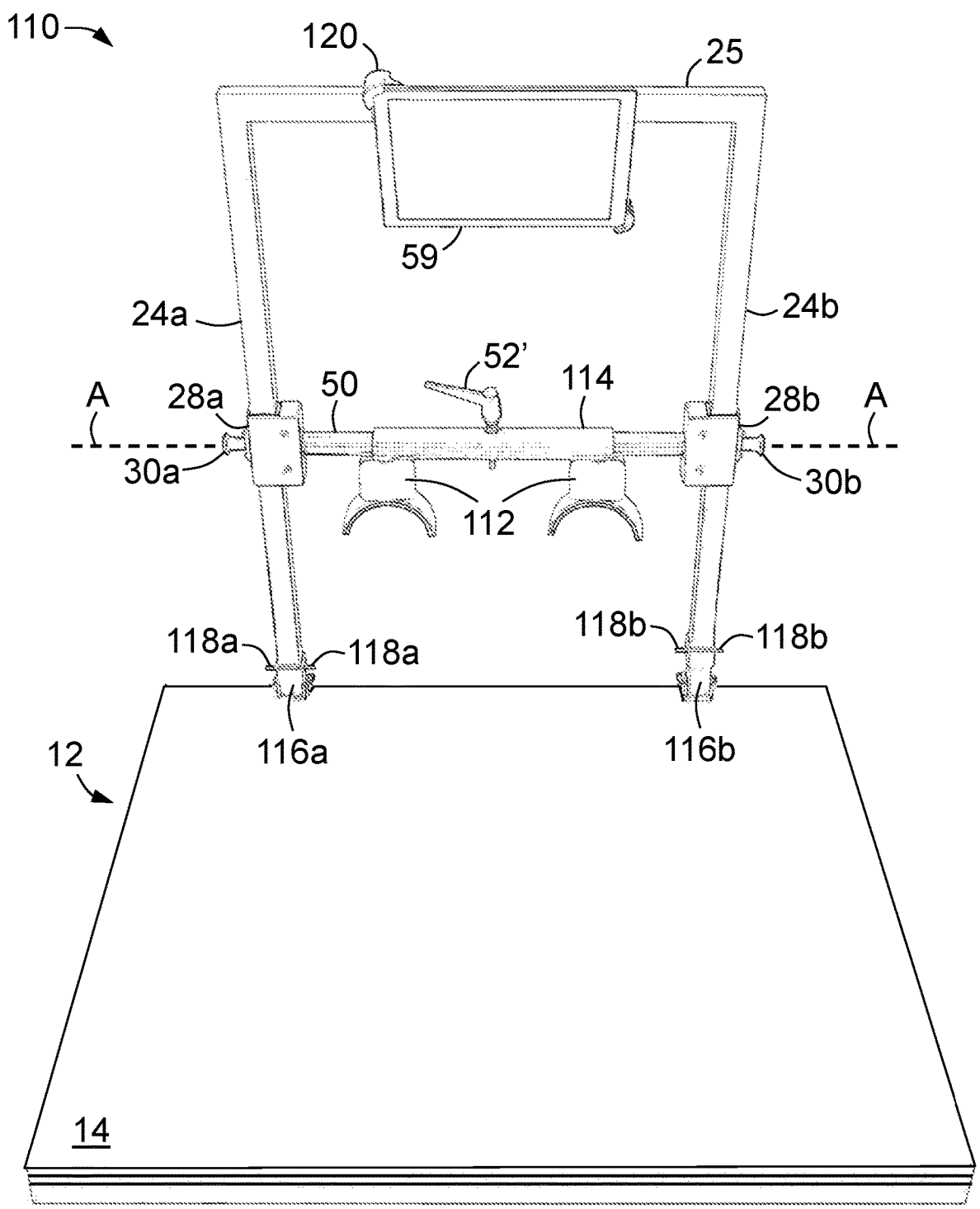
FIG. 15 is a front perspective view of an instrumented strength testing and training apparatus according to a third alternative embodiment of the invention.

FIGS. 13 to 15 are front perspective views of instrumented strength testing and training apparatuses 90, 100, 110 according to three alternative embodiments of the invention. Many features of apparatuses 90, 100, 110 are identical or similar to comparable features of apparatus 10 of FIG. 1, and like reference numerals have been used to identify like features. It should also be appreciated that the distinctive features of the embodiments of FIGS. 13 to 15 (and indeed those of the embodiments of FIGS. 1 and 10) may be mixed as desired when technically feasible.

In the embodiments of FIGS. 13 to 15, upright members 24a, 24b are generally straight while, in apparatus 90 of FIG. 14, upright frame 20 has curved corners 92a, 92b where upright members 24a, 24b meet handle 25.

In apparatus 90 of FIG. 13, force sensors 42a, 42b, 42c—used for measuring force applied perpendicular to rotational axis A—are located on the back of instrument unit 22; this allows force sensors 42a, 42b, 42c to be used at a higher position without the need for bent upright members 24a, 24b. In apparatus 100 of FIG. 14, force sensors 42a, 42b, 42c are located—for similar considerations—on the front of instrument unit 22, so are not shown in FIG. 14 (instrument unit 22 being essentially inverted in that view).

In apparatuses 90, 100 of FIGS. 13 and 14, instrument unit 22 is rotatable to allow force to be measured in the same manner as is instrument unit 22 of apparatus 10 of FIG. 1, in the latter's various configurations.

In apparatus 100 of FIG. 14, instrument unit 22 is supported by horizontal bar 50', which is supported by sleeves 28a, 28b which are supported by respective upright members 24a, 24b. However, in this embodiment, horizontal bar 50' terminates in flat plates 102a, 102b that are received by slots in the inner faces of sleeves 28a, 28b. This facilitates the mounting and demounting of instrument unit 22 from sleeves 28a, 28b when desired.

Apparatus 110 of FIG. 15 includes distributed instrumentation that includes a plurality of detachable force sensors 112; each force sensor 112 has on-board load cell, rechargable battery, microcontroller, Micro-USB port or the like, power button (not shown) and display (such as an LCD display) or indicator (such as an LED indicator, not shown). Thus, although distributed, the instrumentation of apparatus 110 is nonetheless validly schematically represented by FIG. 4, and each of sensors 112 is in data communication with an associated computing device via a wired or wireless connection, in the same manner as is instrument unit 22 of the embodiments described above.

Force sensors 112 of apparatus 110 may be detachably attached to apparatus 110 at different locations and in different orientations in order to support the measurement of force in any number of directions, as described below. The sensors may be attached by a detent pin quick-release mechanism, or by a threaded bolt mechanism or the like.

For example, apparatus 110 may be configured with sensors 112 attached to horizontal bar 50, as shown in FIG. 15, in order to measure force applied perpendicularly to rotational axis A of bar 50. As in the other embodiments, sensors 112 can be rotated about rotational axis A of horizontal bar 50 (such as by rotating sensors 112 relative to horizontal bar 50 or by rotating horizontal bar 50), to allow the force to be applied in any of a plurality of directions.

Force sensors 112 may be attached to horizontal bar 50 by any suitable mechanism. In the illustrated example, apparatus 110 includes a rotatable mount in the form of a rotatable sleeve 114 located on horizontal bar 50. Rotatable sleeve 114 includes an attachment mechanism, such as mounting points or bolts, for attaching one or more of force sensors 112 to rotatable sleeve 114 and hence to horizontal bar 50. In apparatus 110 of FIG. 15, the rotational position of rotatable sleeve 114 (and hence of force sensors 112 mounted thereon) is locked using a screw tightening mechanism 52' (cf. locking pin 52 of FIG. 3). Screw tightening mechanism 52' may, as in the illustrated example, pass through holes (not shown) in horizontal bar 50, these holes defining a fixed plurality of possible rotational orientations. In another example, screw tightening mechanism 52' frictionally engages horizontal bar 50, so that rotatable sleeve 114 may be given essentially any rotational orientation.

Apparatus 110 includes further sleeves 116a, 116b that are supported by and slidably adjustable in position along upright members 24a, 24b. Further sleeves 116a, 116b may be locked at a desired position on with sprung height locking pins (not shown) that are received by locating holes (not shown) on the rear surfaces of upright members 24a, 24b. Sleeves 116a, 116b are each provided with one or more (in this example, two) attachment points 118a, 118b for supporting force sensors 112.

Sensors 112 may be detachably attached to respective sleeves 116a, 116b, on either side thereof. For example, force sensors 112 may be attached to inwardly facing attachment points 118a, 118b, such that the sensor pads of force sensors 112 are directed towards the centre line of upright frame 20 and hence each other. With apparatus 110 configured with sensors 112 attached to the inside of further sleeves 116a, 116b, the sensors can measure force applied parallel to rotational axis A of bar 50 and hence away from the centre line of upright frame 20. As in other embodiments, measuring force in this axis is used in a number of specific protocols, including bilateral supine hip abduction where applying the force in opposing directions allows the user to self-stabilise.

In another example, force sensors 112 may be attached to outwardly facing attachment points 118a, 118b, such that the sensor pads of force sensors 112 are directed away from the centre line of upright frame 20 and hence away from each other.

In one example, apparatus 110 is configured with a sensor 112 attached to the inside of further sleeve 116a and a sensor 112 attached to the outside of the same further sleeve 116a. In this configuration, sensors 112 attached to further sleeve 116a can measure force applied parallel to rotational axis A of the horizontal bar and towards the upright member 24a (and thus towards each other). As with the other embodiments, measuring force in this axis is used in a number of specific protocols, including bilateral supine hip adduction where applying the force in opposing directions allows the user to self-stabilise.

It will be appreciated that any of the above embodiments may include the associated computing device, rather than merely cooperating with an external computing device, and this is the case in the embodiment of FIG. 15. Thus, apparatus 110 includes a computing device 59 in the form of a tablet computer, mounted to handle 25 for ease of viewing and operation by the user with a clamp or bracket 120. Computing device 59 includes the software 60, as described above, and communicates wirelessly with each of force sensors 112.

As discussed above, locking pins 26 are used to fix and remove upright frame 20 from either folding hinged mounts 61 of apparatus 10 (cf. FIG. 1) or floor mounts 82a, 82b of apparatus 80 (cf. FIG. 10). In apparatuses 90, 100 of FIGS. 13 and 14, upright frame 20 is fixed to base 12 so locking pins are not required; however, upright frame 20 is pivotably attached to base 12, so upright frame 20 can be folded down over base 12. In apparatus 110 of FIG. 15, upright frame 20 is attached to base 12 with bolts or pins (not shown) which can be removed to detach upright frame 20 from base 12 when desired.

Top panel 14 of apparatus 90 of FIG. 13 is, like top panel 14 of apparatus 10 of FIG. 1, removable. In apparatuses 100, 110 of FIGS. 14 and 15, top panel 14 is fixed to base 12.

Modifications within the scope of the invention may be readily effected by those skilled in the art. It is to be understood, therefore, that this invention is not limited to the particular embodiments described by way of example hereinabove.

In the claims that follow and in the preceding description of the invention, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

Further, any reference herein to prior art is not intended to imply that such prior art forms or formed a part of the common general knowledge in any country.

The invention claimed is:

1. A testing and training apparatus, comprising:
   an upright frame including two upright members;
   an instrumentation support that is supported by the upright frame via attached bracket sleeves, the bracket sleeves located on respective upright members of the two upright members, wherein the instrumentation support is rotatably coupled to the bracket sleeves thereby enabling rotation of the instrumentation support with respect to the bracket sleeves when supported by the upright frame, the rotation being about a horizontal axis extending in a direction between the two upright members, the instrumentation support selectively lockable against further rotation; and
   the instrumentation support comprising instrumentation comprising a plurality of force sensors,
   wherein the bracket sleeves are adjustable in position on the upright frame to enable a vertical movement of the instrumentation support with respect to the upright frame and are lockable at a desired position, the vertical movement being independent of the rotation of the instrumentation support.

2. The apparatus of claim 1, wherein the apparatus is controllable to output data signals indicative of force detected by each of the force sensors.

3. The apparatus of claim 1, wherein the horizontal axis extends in a direction that is parallel to a direction of elongation of the instrumentation support.

4. The apparatus of claim 1, wherein the instrumentation support comprises a control panel, a plurality of load cells, a battery, and/or a microcontroller and a data communication bus.

5. The apparatus of claim 1, wherein the instrumentation is distributed, each of the force sensors comprising a control panel, a load cell, a battery, and/or a microcontroller and a data communication bus.

6. The apparatus of claim 1, wherein the instrumentation is configured to selectively activate one or more of the force sensors according to a desired testing or training regime.

7. The apparatus of claim 1, wherein the instrumentation is controllable with a computing device when in data communication with the instrumentation.

8. The apparatus of claim 7, further comprising the computing device.

9. The apparatus of claim 1, wherein at least one force sensor is mounted to the instrumentation support and arranged to receive a force in a direction substantially parallel to another mounted force sensor.

10. The apparatus of claim 1, wherein at least one force sensor is mounted to the instrumentation support and arranged to receive a force in a direction substantially perpendicular to another mounted force sensor.

11. The apparatus of claim 1, wherein a force sensor is moveable between a first position and a second position on the apparatus.

12. The apparatus of claim 1, further comprising a controller configured for data communication with a computing device, wherein the controller is interfaced with the plurality of force sensors.

13. The apparatus of claim 12, wherein the controller is controllable by the computing device to selectively receive signals from one or more of the plurality of force sensors and to communicate an indication of the forces received by the selected one or more force sensors.

14. The apparatus of claim 1, wherein the instrumentation is configured to output data signals indicative of force detected by the force sensors.

15. A testing or training method, comprising:
   locating a plurality of force sensors with an instrumentation support on an upright frame at a height selected according to a desired testing or training exercise, wherein the upright frame comprises two upright members, and wherein the instrumentation support is supported by the upright frame via attached bracket sleeves, the bracket sleeves locatable on respective upright members of the two upright members and adjustable in position on the upright frame to enable a vertical movement of the instrumentation support with respect to the upright frame and are lockable at a desired position, wherein the instrumentation support is rotatably coupled to the bracket sleeves thereby enabling rotation of the instrumentation support with respect to the bracket sleeves when supported by the upright frame, the rotation being about a horizontal axis extending in a direction between the two upright members and independent of the vertical movement of the instrumentation support;
   rotating the instrumentation support about the horizontal axis to select a rotational orientation according to the desired testing or training regime, the horizontal axis extending in a direction between the two upright members;
   locking the instrumentation support at said rotational orientation to prevent further rotation about the horizontal axis;
   conducting the testing or training exercise at the selected height and rotational orientation; and
   generating data signals indicative of force detected by the force sensors during the testing or training exercise.

16. The method of claim 15, comprising, subsequent to conducting the testing or training exercise:
   adjusting the rotational orientation of the instrumentation support in accordance with a further desired testing or training exercise by unlocking the instrumentation support with respect to rotation;
   changing the rotational orientation according to the further desired testing or training exercise;
   relocking the instrumentation support with respect to rotation;
   conducting the further testing or training exercise at the newly selected rotational orientation; and
   generating data signals indicative of force detected by the force sensors during the further testing or training exercise.

17. The method of claim 16, further comprising the step of:
   after conducting the training and testing exercise and before conducting the further training and testing exercise, changing the height of the instrumentation support and locking the instrumentation support at the new height.

18. The method of claim 15, wherein the instrumentation support comprises at least one sensor mounted to receive a force in a direction substantially perpendicular to another mounted sensor.

19. The method of claim 15, further comprising the step of moving a force sensor between a first position and a second position on the apparatus.

20. The method of claim 15, wherein at least one force sensor is mounted to the instrumentation support and arranged to receive a force in a direction substantially parallel to another mounted force sensor.

* * * * *